US008886619B2

(12) United States Patent
Reinke (10) Patent No.: US 8,886,619 B2
(45) Date of Patent: Nov. 11, 2014

(54) STRUCTURED TEST ADHERENCE MANAGEMENT FOR MANUAL DATA ENTRY SYSTEMS (75) Inventor: Robert E. Reinke, Indianapolis, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 120 days.

(21) Appl. No.: 13/448,966

(22) Filed: Apr. 17, 2012

(65) Prior Publication Data

US 2013/0173566 A1 Jul. 4, 2013

Related U.S. Application Data (60) Provisional application No. 61/581,331, filed on Dec. 29, 2011.

(51) Int. Cl.
G06F 17/30 (2006.01)
(52) U.S. Cl.
USPC .......................................... 707/694
(58) Field of Classification Search
CPC ..................................... G06F 19/322
USPC ................................... 707/694
See application file for complete search history.

(56) References Cited

U.S. PATENT DOCUMENTS

| 7,291,107 | B2 | 11/2007 | Hellwig et al. |
| 7,553,281 | B2 | 6/2009 | Hellwig et al. |
| 2004/0172284 | A1 | 9/2004 | Sullivan et al. |
| 2006/0047192 | A1 | 3/2006 | Hellwig et al. |
| 2006/0137695 | A1 | 6/2006 | Hellwig et al. |
| 2007/0230282 | A1 | 10/2007 | May et al. |
| 2008/0058628 | A1 | 3/2008 | Hellwig et al. |
| 2008/0177149 | A1 | 7/2008 | Weinert et al. |
| 2009/0150177 | A1 | 6/2009 | Buck et al. |
| 2010/0016700 | A1 | 1/2010 | Sieh et al. |
| 2010/0069730 | A1 | 3/2010 | Bergstrom |
| 2010/0160757 | A1 | 6/2010 | Weinert et al. |
| 2010/0160759 | A1 | 6/2010 | Celentano et al. |

(Continued)

FOREIGN PATENT DOCUMENTS

WO 2010/089304 8/2010

OTHER PUBLICATIONS

"Glooko App Offers Diabetics Easier Self-Checks", www.phys.org/news/2011-11-glooko-app-diabetics-easier-self-checks.html; (2011).

(Continued)

Primary Examiner — Rehana Perveen
Assistant Examiner — Alexander Khong
(74) Attorney, Agent, or Firm — Harness, Dickey & Pierce, P.L.C.

(57) ABSTRACT

A computer-implemented method is provided for managing manual entries of blood glucose measures for a patient in relation to a structured collection procedure managed by a portable computing device. The method includes: managing a structured collection procedure for a user of the computing device, where the structured collection procedure specifies one or more collection events for obtaining blood glucose measures for a patient; receiving a data entry for a blood glucose measure from the user of the computing device; evaluating the data entry in relation to the structured collection procedure using a membership rule set, where the membership rule set defines rules for associating data entries with structured collection procedures; and inputting the data entry into a logbook residing in a data store on the computing device. Depending upon the evaluation, the data entry may be input with or without an association to the structured collection procedure.

19 Claims, 4 Drawing Sheets (56) References Cited

U.S. PATENT DOCUMENTS

2010/0168660 A1 7/2010 Galley et al.
2010/0198142 A1 8/2010 Sloan et al.
2010/0212675 A1 8/2010 Walling et al.
2010/0218132 A1 8/2010 Soni et al.
2010/0331650 A1 12/2010 Batman
2011/0029870 A1 2/2011 May et al.

OTHER PUBLICATIONS

Glooko Logbook & MeterSync Cable, www.glooko.com/product/logbook , (2011).

STRUCTURED TEST ADHERENCE MANAGEMENT FOR MANUAL DATA ENTRY SYSTEMS

CROSS-REFERENCE TO RELATED APPLICATIONS

This application claims the benefit of U.S. Provisional Application No. 61/581,331, filed Dec. 29, 2011. The entire disclosure of the above application is incorporated herein by reference.

FIELD

The present disclosure relates to systems and methods for assisting patients with chronic diseases in managing structured test procedures, including management of manual data entries received from the patients.

BACKGROUND

For people with diabetes, successful management requires monitoring the effects lifestyle changes can have in both the short term and long term. Regular testing of blood glucose level (bG) is an important way to monitor such effects over shorter time frames. Portable handheld glucose meters and associated test strips have been used for years in both homes and healthcare facilities to obtain blood glucose values.

Patients and healthcare professionals may thereby track and analyze glucose measurements over a period of time to assess changes in the patient over the course of a day, week, or other desirable timeframe. For example, some healthcare professionals may instruct a patient to obtain glucose measurements seven or more times a day over a course of a few consecutive days so that patients may observe the changes associated with particular events or times of day. Structured test procedures are typically administered in an automated manner by the glucose meter. During testing, the patient is prompted to input blood samples into the glucose meter at designated times in accordance with a structured test procedure. Glucose measures derived from the blood samples are in turn properly tagged and associated with the structured test procedure being administered by the glucose meter.

More recently, diabetes management applications have been developed for use independent from a glucose meter. For example, a diabetes management application may reside on a patient's phone or another type of mobile computing device. Such diabetes management applications can likewise help the patient manage structured test procedures by reminding them to collect blood glucose measures and insuring that the collected values obey certain constraints. Unlike glucose meters, glucose measures are input manually by the patient into the diabetes management application. Accordingly, there is a need to properly manage manual data entries received from the patient in relation to the structured test being administered to the patient. This section provides background information related to the present disclosure which is not necessarily prior art.

SUMMARY

In one aspect the present disclosure, a computer-implemented method is provided for managing manual entries of blood glucose measures for a patient in relation to a structured collection procedure managed by a portable computing device. The method includes: managing a structured collection procedure for a user of the computing device, where the structured collection procedure specifies one or more collection events for obtaining blood glucose measures for a patient; receiving a data entry for a blood glucose measure from the user of the computing device; evaluating the data entry in relation to the structured collection procedure using a membership rule set, where the membership rule set defines rules for associating data entries with structured collection procedures; and inputting the data entry into a logbook residing in a data store on the computing device. Depending upon the evaluation, the data entry may be input with or without an association to the structured collection procedure.

In another aspect of the present disclosure, a diabetes management application is presented for use on a portable computing device. The diabetes management application includes: a structured test module that manages a given structured collection procedure for the user of the computing device, where the given structured collection procedure specifies one or more collection events for obtaining blood glucose measures for a patient; an input module configured to receive a given data entry for a blood glucose measure from a user of the computing device; a logbook configured to store data entries related to diabetes care of the patient; a membership rule set that defines rules for associating data entries received from the user with structured collection procedures; and a membership module configured to receive the given data entry from the input module and operable to associate the given data entry with the given structured collection procedure based on the membership rule set, where the input module, the structured test module and the membership module are executed by a computer processor residing on the computing device.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

The drawings described herein are for illustrative purposes only of selected embodiments and not all possible implementations, and are not intended to limits the scope of the present disclosure. Corresponding reference numerals indicate corresponding parts throughout the several views of the drawings.

DETAILED DESCRIPTION

Figure 1:
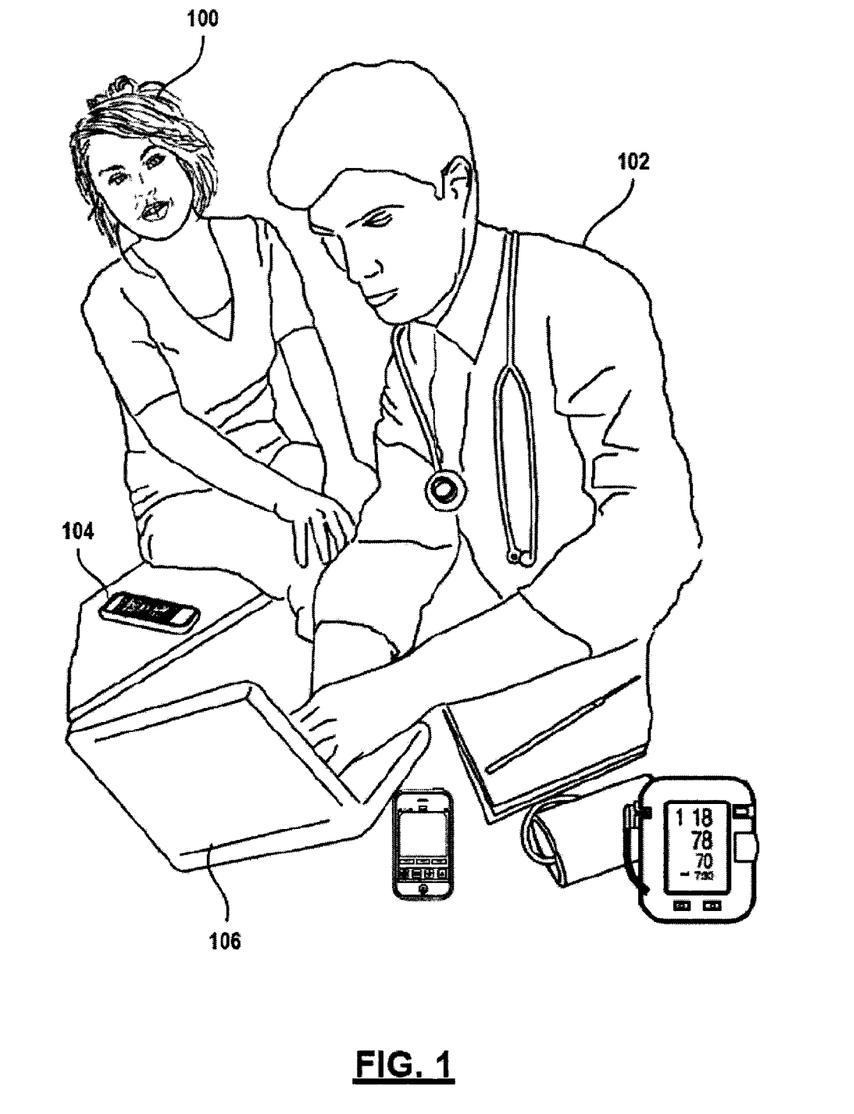
FIG. 1 is a drawing depicting a patient and a treating clinician.

Referring to FIG. 1, a person 100 with diabetes and a healthcare professional 102 are shown in a clinical environment. Persons with diabetes include persons with metabolic syndrome, pre-diabetes, type 1 diabetics, type 2 diabetics and gestational diabetics and are collectively referred to as a patient. Healthcare providers for diabetes are diverse and include nurses, nurse practitioners, physicians, and endocrinologists and are collectively referred to as a clinician. While this disclosure makes reference to diabetes care, it is readily understood that the concepts related to structured testing disclosed herein can be applied to other types of chronic diseases. Likewise, this disclosure makes reference to blood glucose measures but the concepts are extendable to other types of biomarkers of a patient including but not limited to an interstitial glucose value, an HbA1c value, a heart rate measurement, a blood pressure measurement, lipids, triglycerides, cholesterol and the like.

During a healthcare consultation, the patient 100 typically shares with the clinician 102 a variety of patient data including blood glucose measurements, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically by the patient 100 or clinician 102 using a diabetes management application accessible on a handheld portable computing device 104, a personal computer (PC) 106 or some other type of computing device. The clinician 102 can analyze the patient data manually or electronically using the diabetes management application or some other type of diabetes analysis software. After analyzing the patient data and reviewing adherence of the patient 100 to previously prescribed therapy, the clinician 102 can decide whether to modify the therapy for the patient 100.

Figure 2:
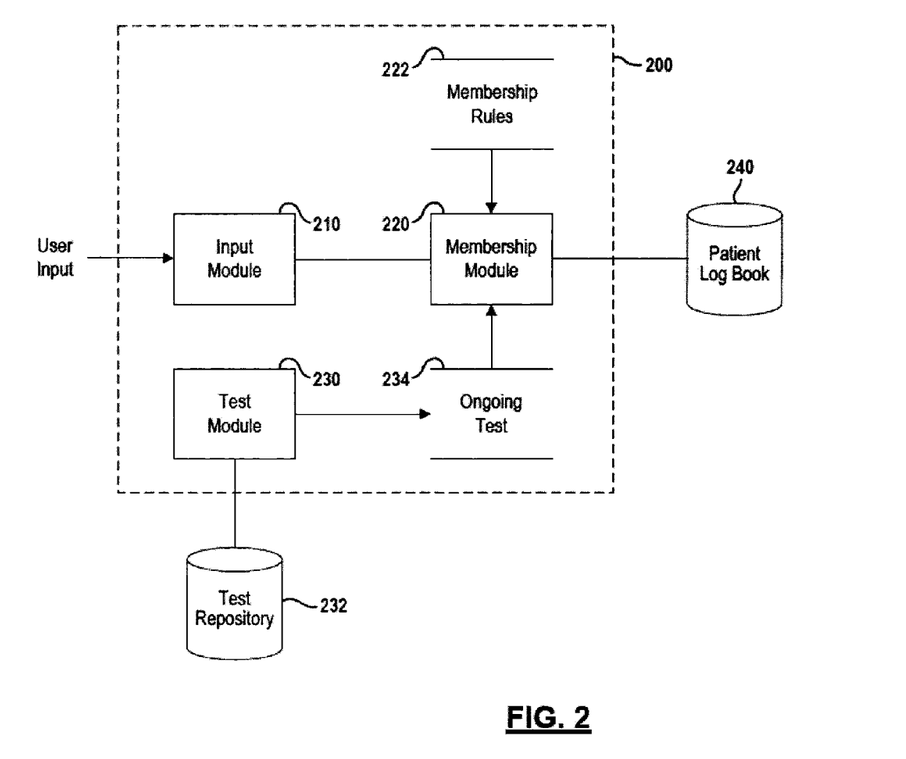
FIG. 2 is a block diagram of an exemplary diabetes management application 200 which may reside on a portable computing device.

FIG. 2 depicts an exemplary diabetes management application 200 which may reside on a portable computing device. The diabetes management application 200 is intended for use by persons with diabetes. Generally, the diabetes management application 200 will support entry, transfer, storage, display and analysis of blood glucose measures and other health indicators. The diabetes management application 200 will also provide structured testing procedures to help the user increase their understanding of how to manage their diabetes. Because people tend to carry their portable computing device (e.g., phone) with them, the diabetes management application 200 will provide persons with diabetes an easy-to-use way to capture and track their health information. Furthermore, the diabetes management application 200 will support data sharing by means of short message service (SMS) as well as email delivery of reports. Data will then be available to the patient's healthcare provider, thereby improving the healthcare provider's ability to help the patient manage their diabetes. Further details regarding an exemplary diabetes management application 200 may be found in U.S. provisional patent application No. 61/581,159 entitled "DIABETES MANAGEMENT APPLICATION FOR MOBILE PHONE" which is filed concurrently herewith and incorporated herein by reference.

In an exemplary embodiment, the diabetes management application 200 may include an input module 210, a membership module 220 and a structured test module 230. The structured test module 230 is operable to manage a structured test or collection procedure to the user of the computing device, where the structured test specifies one or more collection events for obtaining blood glucose measures from a patient. For simplicity of the explanation set forth below, only one structured test is managed at any given time by the structured test module 230 although it is envisioned that other embodiments could support management of more than one structured test. In any case, the structured tests accessible to the structured test module 230 are stored in data store 232 residing on the portable computing device.

For illustration purposes, the diabetes management application 200 supports two exemplary structured tests: the testing in pairs (TiP) structured test and the three-day profile structured test. The testing is pairs test involves obtaining a pair of blood glucose measures in relation to a given event, such as a meal. Specifically, the pair of blood glucose measures for a given test should fall within a window of time which encapsulates the given event, such that a first measure occurs before the given event and the second measure occurs after the given event. Paired testing can address scenarios such as the relationship between portion sizes and postprandial glucose values, the effect of exercise on blood glucose control and the efficacy of insulin doses. On the other hand, three-day profile tests involve obtaining blood glucose measures at predefined time slots throughout the course of a given day and repeating the measures over a three day period. For example, the three-day profile test specifies obtaining blood glucose measures at seven different times during the day: pre-breakfast; post-breakfast; pre-lunch; post-lunch; pre-dinner; post-dinner; and bedtime. While reference is made throughout this disclosure to these two particular structured tests, it is readily understood that the concepts disclosed herein are extendable to other types of structured tests.

During administration of a given structure test, the input module 210 is configured to receive data entries from a user of the computing device. For example, a data entry may be for a blood glucose measure taken by the user, where the data entry includes a blood glucose measure along with a date and time at which the blood glucose measure was taken. It is readily understood that the data entry may further include other data related to the blood glucose measure and/or the patient. In other examples, a data entry may not include a blood glucose measure. Rather, the data entry may pertain to a meal event, an exercise event or other types of events or health parameters related to the patient (also referred to herein as non-blood glucose entries). In any case, one or more parameters of the data entry are input manually by the user of the computing device.

The membership module 220 is configured to receive the data entries from the input module 210 and evaluates the data entries for association with the structured test procedure currently being managed by the structured test module 230. More specifically, the data entries are evaluated in relation to a set of membership rules 222, where the set includes rules for associating data entries with the given structured collection procedure as will be further described below. Data entries are in turn input by the membership module into a logbook 240 for the patient with or without an association to the given structured collection procedure. Membership rules may also be stored in a data store residing on the portable computing device.

Three fundamental issues unique to manual-entry systems and structured testing are: (1) the user can set or change the date and time of logged events; (2) entries can be independent of blood glucose values; and (3) existing entries can be deleted. These issues create substantial problems for structured test management. The central idea behind structured testing is that measuring blood glucose in a structured (as opposed to ad-hoc) way can give patients and healthcare providers key insights into improving the patient's diabetes management. To complete a structured test, the user must therefore measure their blood glucose at specific times relative to certain events. It is because timing of blood glucose measurements is so important that the extra flexibility of the manual-entry system causes problems. In a blood glucose meter, it is relatively clear whether a given measurement meets the criteria for inclusion in a structured test because the meter actually records the blood glucose value and its corresponding time (from the device's clock). In a manual-entry device, however, the situation is much more fluid and difficult to manage.

Problems associated with manual-entry devices are best illustrated by an example. Suppose the user is executing a Testing in Pairs (TiP) structured test associated with exercise event. The TiP test specifies that the trigger in the exercise event and that the post-exercise blood glucose measure must occur in a 60 minute window after the event. But consider the following reasonable scenario:

1. The structured test began on Sunday
2. On Monday morning, the user measured their blood glucose at 6:30 AM. They took a half-hour walk from 7 to 7:30, and measured their blood glucose again at 10 AM. They recorded none of this in diabetes management application.
3. On Tuesday evening, the user remembers that they didn't log their Monday exercise and related blood glucose measures. They open the diabetes management application and scroll their meter's memory to record the blood glucose at 6:30, record the exercise at 7:00 and use their meter to get the blood glucose at 10. But, since it is now Tuesday, they neglect to reset the date on these events. As far as the diabetes management application is concerned, the events occurred on Tuesday morning, not Monday morning.
4. On Wednesday, when the user logs some something else, they realize the mistake and reset the dates on the three earlier events (from Tuesday to Monday).

Now consider the following five questions:

1. When the user enters the first blood glucose value, should the diabetes management application consider it part of the structured test? Should it allow the user to identify it as such? This is not at all obvious because no exercise has been entered.
2. On Wednesday, the user resets the time of the exercise by a day. At that moment the post-exercise blood glucose is outside the acceptance window for the post event. What happens?
3. What happens if the user makes a blood glucose entry between 6:30 and 10 and tries to include it in the structured test?
4. What happens if the user, when they move the post-exercise blood glucose reading, mistakenly changes the time to 10 PM (outside the allowable range)?
5. What happens if the user, after moving the 6:30 AM event but before moving the 10 AM event, creates a new pre-exercise event at 7 AM on Tuesday?

This disclosure presents an analysis of the problem of structured test membership in a manual-entry situation and solutions in light of this analysis.

Before considering possible solutions, a way is needed to describe the problems and issues that could arise with respect to structured testing in a manual-entry system. Such a description is necessary to have confidence that a proposed solution will actually work and not leave open issues. The previous section identified three aspects unique to manual-entry systems: editable date/time, non-blood glucose entries, and the ability to delete existing entries. As a first step toward simplifying the problem, data entries are assumed to be blood glucose measures. While other types of data entries are ignored for the analysis set forth below, it is readily understood that the analysis (including membership rules) could be extended to other types on non-blood glucose entries. As a second step towards simplifying the analysis, it is noted that editing an existing logbook record is conceptually equivalent to deleting the original record and creating a new record with the changed values. Therefore, this analysis need only consider creating new records and deleting existing records. Finally, the analysis is applied to Testing in Pairs (TiP) testing and Three-day Profile (3DP) testing separately because they are very different in terms of their requirements and constraints. Again, it is envisioned that this type of analysis can be extended to other types of structured tests With respect to a Testing in Pairs regimen, there is only a need to address a regimen that is in progress; completed regimens are assumed to be "locked" and cannot be changed. For an in-progress TiP test, each relevant data entry (where relevant means "contains a blood glucose value and occurs after the TiP regimen started") must fall into one of three states:

1. The entry in question is not part of the structured test which is referred to herein as the "OUT" state.
2. The entry in question is potentially half of a pair whose other half is not yet available which is referred to herein as the "SINGLE" state.
3. The entry in question is part of a completed pair which is referred to herein as the PAIRED state.

Possible situations that any solution must address are enumerated as follows:

Deleting an OUT entry
Deleting a SINGLE entry
Deleting a PAIRED entry
Creating a relevant new entry in the presence of existing entries The last of these requires further expansion: what are the meaningful possible combinations of structured tests in the "presence" of a new entry? The time limits on TiP pairs give us a way to answer this. Each TiP test has an acceptance time "window" in which a TiP pair can occur. For example, the time window for a TiP test pertaining to an exercise event is 6 hours. Let w be the maximum time window for the type of TiP in progress. Then, for a new logbook entry at time t, we need only concern ourselves with existing logbook entries in the time interval [t−w, t+w]. With respect to this interval, note that "OUT" entries are not relevant—they do not affect the state of the new entry. Therefore, potential solutions need only deal with the following situations:

There are no PAIRED or SINGLE entries in the window
There are no PAIRED entries in the window, and one SINGLE entry
There are no PAIRED entries in the window, and more than one SINGLE entry
There is a PAIRED entry in the window, but no SINGLE entries
There is one PAIRED entry and one SINGLE entry in the window
There is one PAIRED entry and more than one SINGLE entry in the window
There are multiple PAIRED entries and no SINGLE entries in the window
There are multiple PAIRED entries and one SINGLE entry in the window
There are multiple PAIRED and multiple SINGLE entries in the window Note that in the above, it is sufficient for one member of a pair to fall in the window to count as a single PAIRED entry in the window. Added to the three earlier scenarios (for delete), twelve possible scenarios have been identified that can occur in a manual-entry system with respect to a running TiP regimen. Potential solutions must address every one of these situations, either by providing explicit rules for dealing with it, or explicit rules for precluding it.

The question at hand is how to manage membership of logbook entries in a structured test. It is not really an option to have the user manage membership with no enforcement of restrictions; that would defeat the purpose of structured testing. There are two possible general approaches. First, allow the user to manage membership of logbook entries in a structured test, with guidance and restriction by the system. This approach is referred to as the explicit management approach. Second, automatically determine membership based on defined criteria. This approach is referred to as the implicit management approach. Under either approach, constraints and rules must be identified that insure that all of the situations identified in the problem analysis set forth above are met.

Starting with the explicit management approach, membership rules are further developed for a TiP test. The primary issue in the explicit approach is providing simple and clear restrictions so that the user is not confused when the system has to reject an attempt to associate a data entry with the structured test. Three global constraints are sufficient to insure that the explicit approach works correctly for TiP test. The three global constraints are as follows:

CE1: Only one SINGLE allowed at a time
CE2: Pairs cannot overlap or be nested.
CE3: Pairs must be started in chronological order Guided by these three global constraints, particular membership rules can be enumerated for each of the twelve possible scenarios. These membership rules collectively define the membership rule set which pertains to a TiPs test under the explicit approach and are set forth in the table below.

| Situation | Explicit Approach Logic |
| --- | --- |
| S1: Deleting an OUT entry | Allow |
| S2: Deleting a SINGLE entry | Allow |
| S3: Deleting a PAIRED entry | Per CE1, if there are existing SINGLEs, do not allow. Otherwise, allow and set the remaining entry to SINGLE. |
| S4: Create, no paired or single entries in the window | Allow |
| S5: Create, there is one SINGLE entry in the window | Per CE1, if the new entry and the existing SINGLE make a pair, allow and set both to PAIRED. Otherwise, do not allow per CE1 |
| S6: Create, there are no PAIRED and multiple SINGLE entries in the window | Precluded by CE1 |
| S7: Create, there is a PAIRED entry in the window but no SINGLE entry | Per CE1, if there are existing SINGLEs anywhere, do not allow. Per CE2, if the new entry is between the existing PAIR, do not allow. Otherwise, set the new entry to SINGLE |
| S8: Create, there is a PAIRED entry and a SINGLE entry in the window | Per CE1, if the existing SINGLE and the new entry do not make a pair, do not allow. Per CE2, if the new entry falls within the existing pair, do not allow. Otherwise, pair the new entry and the existing SINGLE and set both to PAIRED |
| S9: Create, there is a PAIRED entry and multiple SINGLE entries in the window | Precluded by CE1 |
| S10: Create, multiple PAIRED entries and no SINGLE entries in the window | Per CE2, if the new entry falls within one of the existing pairs, do not allow. Per CE3, if the new entry falls before either of the existing pairs, do not allow. Per CE1, if there are existing SINGLEs anywhere, do not allow. Otherwise, allow and set the new entry to SINGLE |
| S11: Create, multiple PAIRED entries and one SINGLE entry in the window | Per CE2, if the new entry falls within one of the existing pairs, do not allow. Per CE3, if the new entry falls before either of the existing pairs, do not allow. Per CE1, if the new entry and existing single do not make a pair, do not allow Otherwise, pair the new entry and the existing single, setting both to PAIRED |
| S12: Create, multiple PAIRED entries and multiple SINGLE entries in the window | Precluded by CE1 |

Manual data entries can be evaluated in relation this membership rule set by the membership module 220 in the manner further described below.

The primary issue in the implicit approach is somewhat different from the explicit approach. In the implicit management approach, it is important to leave options open and await further actions by the user. Therefore, in the implicit approach we employ the following constraints:

CI1: Pairs cannot overlap or be nested.

From this constraint, particular membership rules for the implicit approach can be enumerated for each of the twelve possible scenarios. These membership rules collectively define the membership rule set which pertains to a TiPs test under the implicit approach and are set forth in the table below.

| Situation | Implicit Approach Logic |
| --- | --- |
| S1: Deleting an OUT entry | Allow |
| S2: Deleting a SINGLE entry | Allow |
| S3: Deleting a PAIRED entry | Set the remaining entry to SINGLE and apply the logic for a new entry to it. |
| S4: Create, no paired or single entries in the window | Set the new entry to SINGLE |
| S5: Create, there is one SINGLE entry in the window | If the new entry and the existing SINGLE make a pair, set both to PAIRED. Otherwise, make the new entry SINGLE. |
| S6: Create, there are no PAIRED and multiple SINGLE entries in the window | If the new entry can be paired with one of the existing singles, pair it with the SINGLE that encompasses the largest window less than w and set any SINGLE entries that fall within this window to OUT per CI1. Otherwise, set the new entry to SINGLE. |
| S7: Create, there is a PAIRED entry in the window but no SINGLE entry | Per CI1, if the new entry is between the existing PAIR, make the new entry OUT. Otherwise, set the new entry to SINGLE |
| S8: Create, there is a PAIRED entry and a SINGLE entry in the window | Per CI1, if the new entry falls within the existing pair, make the new entry OUT. If the new entry and the existing SINGLE for a pair, set both to PAIRED Otherwise, set the new entry to SINGLE |
| S9: Create, there is a PAIRED entry and multiple SINGLE entries in the window | Per CI1, if the new entry falls within the existing pair, make the new entry OUT. If the new entry can be paired with one of the existing singles, pair it with the SINGLE that encompasses the largest window less than w and set any SINGLE entries that fall within this window to OUT per CI1. Otherwise, set the new entry to SINGLE |
| S10: Create, multiple PAIRED entries and no SINGLE entries in the window | Per CI1, if the new entry falls within one of the existing pairs, set the new entry to OUT. Otherwise, set the new entry to SINGLE |

-continued

| Situation | Implicit Approach Logic |
|---|---|
| S11: Create, multiple PAIRED entries and one SINGLE entry in the window | Per CI1, if the new entry falls within one of the existing pairs, set the new entry to OUT. If the new entry matches the existing SINGLE but the resulting pair intersects an existing pair, set the new entry to OUT. If the new entry matches the existing SINGLE and the resulting pair does not intersect an existing pair, set the new entry and the existing SINGLE to PAIRED. Otherwise, set the new entry to SINGLE |
| S12: Create, multiple PAIRED entries and multiple SINGLE entries in the window | Per CI1, if the new entry falls within one of the existing pairs, set the new entry to OUT. If the new entry matches an existing SINGLE but the resulting pair intersects an existing pair for all such SINGLEs, set the new entry to OUT. If the new entry matches an existing SINGLE and the resulting pair does not intersect an existing pair, choose the SINGLE that encompasses the largest window less than w and set any SINGLE entries that fall within this window to OUT per CI1. Set the new entry and the matching SINGLE to PAIRED. Otherwise, set the new entry to SINGLE |

Manual data entries can be evaluated in relation to this membership rule set by the membership module 220 in the manner further described below.

Turning to the Three-day profile (3DP) regimen, there is only a need to address a structured test that is in progress as was the case with TiP regimen. Thus, completed tests are assumed to be "locked" and cannot be changed. In one regard, 3DP tests are simpler than TiP tests because there are predefined time slots and each time slot has specific requirements. In another regard, 3DP tests are more complex than TiP tests because there is no simplifying concept like "pair" which can reduce the problem analysis space (the concept of "day" in 3DP at first looks like it might be useful, but because a 3DP day has no real relationship to a calendar day, that proves to not be true). Nonetheless, a 3DP regimen can be analyzed in terms of "windows" similar to those used for TiPs tests. Each of the 7 "slots" in a 3DP day has time constraints based on "normal" meal and bed times that the user selects. For example, the user may have indicated that breakfast normally occurs at 7 am. To map a data entry for an event to a slot, the event should fall within a defined time-window associated with the slot (e.g., within 30 minutes of the designated meal time). Additionally, the event should meet the other criteria for the slot. For example, the data entry may specify an indicator for the slot (e.g., pre-breakfast, post-breakfast, pre-lunch, etc.). To map the data entry to a slot, the indicator should also match the indicator associated with the slot. Other types of criteria are also contemplated by this disclosure. When each of the criteria for the slot is met, the data entry is mapped to the slot and thus associated with the structured test. Accordingly, each data entry for a 3DP regimen falls into one of two states:
1. The entry in question is not part of the structured test; referred to herein as the OUT state.
2. The entry in question is filling a slot in the structured test; referred to herein as the SLOTTED state.

The various create and delete scenarios are now enumerated based on the possible states. Delete is straightforward: deleting either an OUT entry or a SLOTTED entry. With respect to a new relevant entry, the following situations are possible:
The entry does not match any slot
The entry matches a slot that has a SLOTTED entry
The entry matches a slot for which there is no SLOTTED entry.

Thus, for 3DP there are only five possible scenarios a solution must address or preclude.

Membership rules for the three-day profile test are considerably simpler because of its division into days and "slots" (corresponding to meal times and bedtimes). Only two global constraints are sufficient for both the implicit and explicit approaches.
C3DP1: Only one entry per slot
C3DP2: Every entry must match a slot Guided by these global constraints, particular membership rules can be enumerated for each of the possible scenarios. These membership rules collectively define the membership rule set which pertains to a 3DP test and are set forth in the table below.

| Situation | Explicit Approach | Implicit Approach |
|---|---|---|
| Delete an OUT entry | Allow | Allow |
| Delete a SLOTTED entry | Allow | Allow |
| New entry does not match any slot | Do not allow per C3DP2 | Make new entry OUT |
| New entry matches a slot for which there is a SLOTTED entry | Do not allow per C3DP1 | Make new entry OUT |
| New entry matches a slot for which there is no SLOTTED entry | Put entry in the slot, make it SLOTTED | Put entry in the slot, make it SLOTTED |

Manual data entries can be evaluated in relation to these membership rules by the membership module 220 in the manner further described below.

Figure 3:
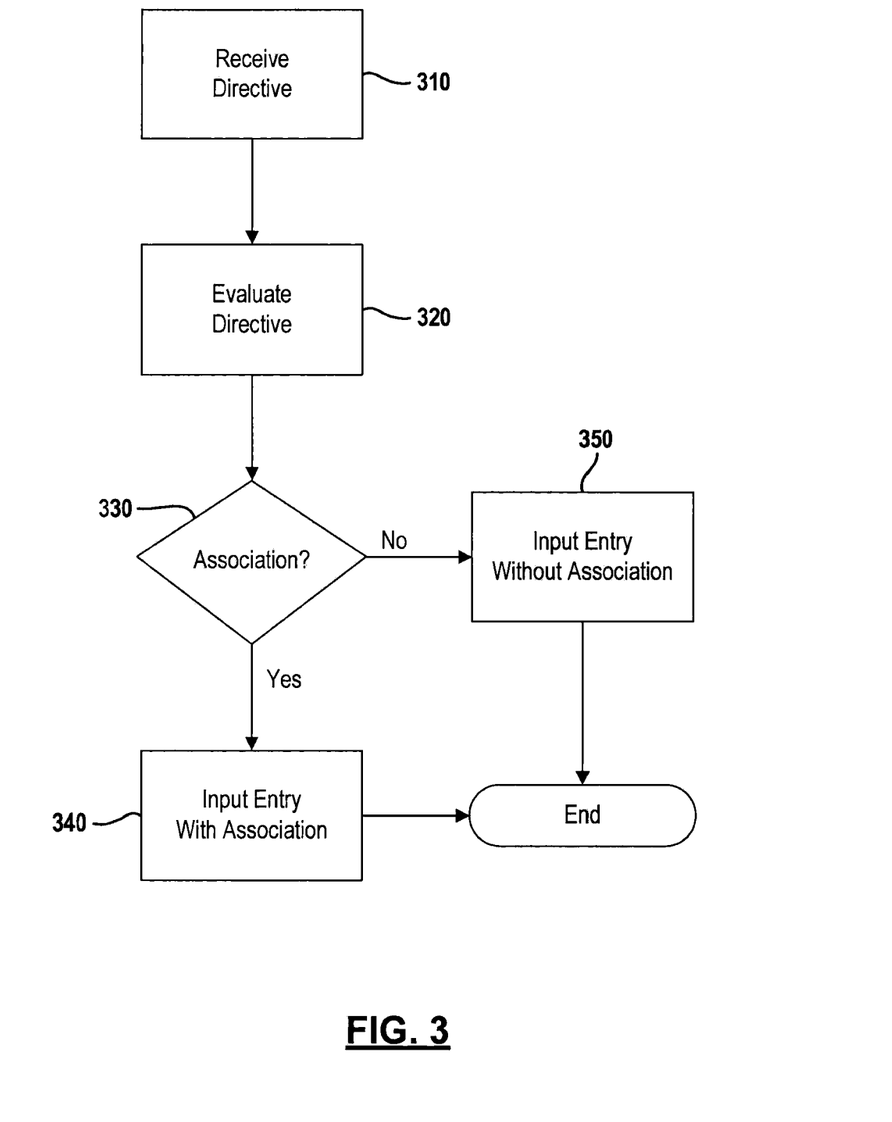
FIG. 3 is a flowchart depicting an exemplary method for managing manual entries of blood glucose measures in relation to a structured test managed by a portable computing device.

FIG. 3 provides an overview of this exemplary method 300 for managing manual data entries of blood glucose measures in the context of a diabetes management application 200 residing on a portable computing device. In an exemplary embodiment, various data related to the patient's diabetes care may be logged by the patient via the diabetes management application 200 into a logbook residing on the portable computing device. For example, during the structured test, the patient may be prompted to manually input data entries for blood glucose measures taken in accordance with the structured test. Such data entries may include blood glucose measures as well as a date and time at which the blood glucose measure was taken by the patient. Of note, this data is provided manually by the patient as opposed to being generated or otherwise provided automatically by the diabetes management application 200. The patient may also input data entries which are unrelated to the ongoing structured test. For example, the patient may input a data entry pertaining to a meal, exercise or some other type of health data. In this case, the data entries are not in response to or associated with the ongoing structure test but nonetheless captured by the diabetes management application 200.

In operation, the diabetes management application 200 is configured to receive directives pertaining to data entries in the logbook as indicated at 310. Directives may include but are not limited to creating, deleting or updating data entries in the logbook. Thus, each directive pertains to one or more particular data entries whether it be deleting an existing data entry or creating a new data entry. Directives are evaluated at 320 using membership rules to determine whether the directive is permissible or not as it relates to the ongoing structured test. In the case of creating a new data entry in the logbook, the data entry may be created with an association to the structured test as indicated at 340 or without an association to the structured test as indicated at 350.

Figure 4:
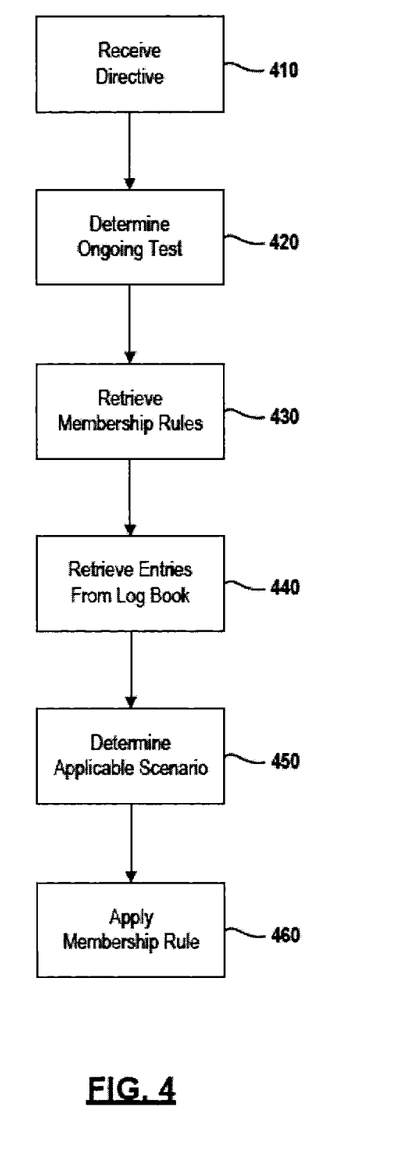
FIG. 4 is a flowchart depicting an exemplary method for evaluating data entries implemented by a membership module of the diabetes management application.

FIG. 4 further depicts the evaluation process as implemented by the membership module 220 of the diabetes management application 200. Upon receiving a directive at 410 from the user, the membership module 220 first determines the type of structured test that is being managed for the patient. In an exemplary embodiment, each structured test may have a unique type identifier (e.g., type 1=TiP, type 2=3DP, etc.). The type identifier for the ongoing structured test may be stored in a data store 234 accessible to the membership module 220, where the data store 234 contains data for the ongoing structure test and is maintained by the test module 230. In this way, the membership module 220 may determine the type of structured test by retrieving the type identifier from the data store 234.

Membership rules vary depending on the management approach and the type of structured test. In an exemplary embodiment, the management approach (i.e., implicit or explicit) may be a preconfigured parameter of the device or a user configurable parameter accessible to the membership module 220. Accordingly, a set of membership rules should be provided for each unique combination of management approach and test type that is supported by the diabetes management application 200. Given the management approach setting and the retrieved test type, the membership module 220 can retrieve at 430 an applicable set of membership rules for evaluating the user directive.

Next, the membership module 220 retrieves at 440 any previous data entries stored in the logbook and associated with the ongoing structured test. In an exemplary embodiment, each structured test administered by the test module 230 is assigned a unique test identifier. The unique test identifier for the ongoing structured test is in turn maintained in the data store 234 by the test module 230. When logging data entries into the logbook, the membership module 220 can access the test identifier for the ongoing structure test and, if applicable, tag the data entries being entered into the logbook with the unique identifier for the ongoing structure test. To retrieve data entries for the ongoing structure test, the membership module 220 can likewise retrieve the test identifier from the data store 234 and, using the retrieved test identifier, retrieve any previous data entries associated with the ongoing structure test from the logbook 240.

From the user directive and the retrieved data entries, the membership module 220 can then determine at 450 the applicable scenario from a set of possible scenarios. For example, assume a directive to create a new data entry in the context of an ongoing TiP test. Should the membership module 220 retrieve one SINGLE data entry in the time window for the ongoing TiP test, the membership module 220 would deem the situation S5 (see scenario table above) and in turn retrieve the corresponding membership rule which applies to this scenario.

Lastly, the membership module 220 applies the corresponding membership rule as indicated at 460. Continuing with the example above, if the new entry and the existing entry meet the pairing criteria for forming a pair, the membership module 220, operating in accordance with the explicit approach, would permit the new entry to be paired with the existing entry and thus associated with the ongoing TiPs test. If the new entry and the existing entry failed to meet the pairing criteria, the membership module 220, operating in accordance with the explicit approach, would tell the user the that the entry cannot be part of the structured test, and ask the user to either modify the entry or remove it from the structured test. In contrast, the membership module 220, operating in accordance with the implicit approach, would permit the new entry to be paired with the existing entry if the new entry and the existing entry meet the pairing criteria for forming a pair. On the other hand, if the new entry and the existing entry failed to meet the pairing criteria, the membership module 220, operating in accordance with the implicit approach, would not associate the new data entry with the ongoing TiP test and permit entry into the logbook. It is to be understood that the pairing criteria are defined by the structured test and thus operate independent from the membership rules set forth in this disclosure. It is to be further understood that only the relevant steps of the membership module 220 are discussed above in relation to FIG. 4, but that other software-implemented instructions may be needed to control and manage the overall operation of the system.

Below the five questions presented above are re-presented with comments describing how the explicit and implicit approaches with the proposed constraints would behave:

1. When the user enters the first blood glucose value, should the diabetes management application consider it part of the structured test? Should it allow the user to identify it as such? This is not at all obvious because no exercise has been entered.

This issue is resolved by the overall assumption that only blood glucose entries are considered. Therefore, in the implicit approach the blood glucose value is SINGLE and in the explicit approach the user has the option (which we presume they select) to include the result in the structured test.

2. On Wednesday, the user resets the time of the exercise by a day. At that moment the post-exercise blood glucose is outside the acceptance window for the post event. What happens?

Presume the user first resets the date on the "before" event (the sequence is the same if the move the "after" event first). In both implicit and explicit approaches, both the "before" the "after" events go to the SINGLE state. Then, when the "before" event is moved, both events return to PAIRED state.

3. What happens if the user makes a blood glucose entry between 6:30 and 10 and tries to include it in the structured test?

This is prohibited in the both the implicit and explicit approaches. In the implicit approach, the new event would be OUT. In the explicit approach, the user would be told they cannot include the result in the structured test.

4. What happens if the user, when they move the post-exercise blood glucose reading, mistakenly changes the time to 10 PM (outside the allowable range)?

In the implicit approach, the new event would be marked SINGLE. In the explicit approach, the user would be told there is an error because there is already a SINGLE event.

5. What happens if the user, after moving the 6:30 AM event but before moving the 10 AM event, creates a new pre-exercise event at 7 AM on Tuesday?

In both approaches, the new event will form a pair with the remaining Tuesday post-exercise. When the user attempts to move that post event, the implicit approach will allow it and set the new event to SINGLE. In the explicit approach, the user will not be allowed to move the post event until providing a pair for the Monday pre event.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A computer-implemented method for managing manual entries of blood glucose measures for a patient in relation to a structured collection procedure administered by a portable computing device, comprising:
   managing, by the portable computing device, a structured collection procedure for a user of the portable computing device, where the structured collection procedure specifies one or more collection events for obtaining blood glucose measures for a patient;
   retrieving a data entry from a logbook residing in a data store on the portable computing device, where the data entry includes a blood glucose measure and a time at which the blood glucose measure was taken, the data entry being in response to the specified one or more collection events;
   presenting the retrieved data entry to the user on a display of the portable computing device;
   receiving a modification to values of the data entry from the user;
   evaluating the modified data entry in relation to the structured collection procedure using a membership rule set, where the membership rule set defines rules for associating data entries with structured collection procedures including adherence of date and time and adherence to a previous data entry; and
   inputting the modified data entry into the logbook.

2. The computer-implemented method of claim 1 further comprises associating the modified data entry with the structured collection procedure in accordance with a rule from the membership rule set.

3. The computer-implemented method of claim 1 further comprises inputting the modified data entry into the logbook without an association to the structured collection procedure in accordance with a rule from the membership rule set.

4. The computer-implemented method of claim 1 wherein a structured collection procedure of a first type specifies a pair of collection events that fall within a window of time which encapsulate a given event, where a first collection event in the pair of collection events occurs before the given event and a second collection event in the pair of collection events occurs after the given event.

5. The computer-implemented method of claim 4 wherein evaluating the data entry further comprises analyzing the data entry only in relation to other data entries in the logbook that fall within the window of time defined for the structured collection procedure of the first type.

6. The computer-implemented method of claim 4 wherein the membership rule set pertaining to the structured collection procedure of the first type includes a first rule that prohibits pairs of collection events from overlapping in time with each other; and
   a second rule that prohibits pairs of collection events from being nested within each other.

7. The computer-implemented method of claim 4 wherein the membership rule set pertaining to the structured collection procedure of the first type includes a first rule that prohibits entry of more than one collection event which is unpaired with another collection event;
   a second rule that prohibits pairs of collection events from overlapping in time with each other;
   a third rule that prohibits pairs of collection events from being nested within each other; and
   a fourth rule that prohibits entry of a given collection event which occurs in time before another pair of collection events.

8. The computer-implemented method of claim 1 wherein a structured collection procedure of a second type specifies a plurality of predefined time slots for obtaining blood glucose measures throughout the course of a given day.

9. The computer-implemented method of claim 8 wherein evaluating the data entry further comprises analyzing the data entry in relation to the plurality of predefined time slots for the structure collection procedure of the second type.

10. The computer-implemented method of claim 8 wherein the membership rule set pertaining to the structured collection procedure of the second type includes a first rule prohibits more than one collection event per time slot; and
    a second rule that requires each data entry associated with the structured collection procedure of the second type to match one of the predefined time slots.

11. A diabetes management application residing on a portable computing device, comprising:
    a structured test module operable to administer a given structured collection procedure to the user of the portable computing device, where the given structured collection procedure specifies one or more collection events for obtaining blood glucose measures for a patient;
    a logbook configured to store data entries related to diabetes care of the patient, the logbook implemented in a data store on the portable computing device;
    an input module configured to present a given data entry to the user on a display of the portable computing device and receive modifications to values of the given data entry from the user, where the given data entry is retrieved from the logbook and includes a blood glucose measure and a time at which the blood glucose measure was taken, a membership rule set that defines rules for associating data entries received from the user with structured collection procedures including adherence of date and time and adherence to a previous data entry, where the membership rule set is stored in a data store on the portable computing device; and a membership module configured to receive the modified given data entry from the input module and evaluate the modified given data entry in relation to the given structured collection procedure using the membership rule set, where the input module, the structured test module and the membership module are executed by a computer processor residing on the portable computing device.

12. The diabetes management module of claim 11 wherein the membership module further operates to input the modified data entry into the logbook, wherein the data entry is associated with the given structured collection procedure.

13. The diabetes management module of claim 11 wherein the membership module further operates to input the modified data entry into the logbook, wherein the data entry is not associated with the given structured collection procedure.

14. The diabetes management module of claim 11 wherein the given structured collection procedure specifies a pair of collection events that fall within a window of time which encapsulate a given event, where a first collection event in the pair of collection events occurs before the given event and a second collection event in the pair of collection events occurs after the given event; and the membership module analyzes the data entry only in relation to other data entries in the logbook that fall within the window of time defined for the given structured collection procedure.

15. The diabetes management module of claim 14 wherein the membership rule set includes a first rule that prohibits pairs of collection events from overlapping in time with each other; and a second rule that prohibits pairs of collection events from being nested within each other.

16. The diabetes management module of claim 11 wherein the membership rule set includes a first rule that prohibits entry of more than one collection event which is unpaired with another collection event;

a second rule that prohibits pairs of collection events from overlapping in time with each other;

a third rule that prohibits pairs of collection events from being nested within each other; and a fourth rule that prohibits entry of a given collection event which occurs in time before another pair of collection events.

17. The diabetes management module of claim 11 wherein the given structured collection procedure specifies a plurality of predefined time slots for obtaining blood glucose measures throughout the course of a given day; and the membership module analyzes the data entry in relation to the plurality of predefined time slots for the structure collection procedure.

18. The diabetes management module of claim 17 wherein the membership rule set includes a first rule prohibits more than one collection event per time slot; and a second rule that requires each data entry associated with the structured collection procedure of the second type to match one of the predefined time slots.

19. A computer-implemented method for managing manual entries of blood glucose measures for a patient in relation to a structured collection procedure administered by a portable computing device, comprising:

managing, by the portable computing device, a structured collection procedure for a user of the portable computing device, where the structured collection procedure specifies one or more collection events for obtaining blood glucose measures for a patient;

receiving, by the portable computing device, a first data entry from the user of the portable computing device, where the first data entry includes a blood glucose measure and a time at which the blood glucose measure was taken, the first data entry being in response to the specified one or more collection events;

evaluating the first data entry in relation to the structured collection procedure using a membership rule set, where the membership rule set defines rules for associating data entries with structured collection procedures including adherence of date and time and adherence to a previous data entry;

inputting the first data entry into a logbook without an association to the structured collection procedure in accordance with a rule from the membership rule set, the logbook residing in a data store on the portable computing device;

receiving, by the portable computing device, a second data entry from the user of the portable computing device, where the second data entry includes a blood glucose measure and a time at which the blood glucose measure was taken, the second data entry being in response to the specified one or more collection events;

evaluating the second data entry in relation to the structured collection procedure using the membership rule set;

inputting the second data entry into the logbook without an association to the structured collection procedure in accordance with a rule from the membership rule set;

receiving, by the portable computing device, a third data entry from the user of the portable computing device, where the third data entry includes a blood glucose measure and a time at which the blood glucose measure was taken, the third data entry being in response to the specified one or more collection events;

evaluating the third data entry in relation to the structured collection procedure using the membership rule set, including evaluating the third data entry in relation to the first and second data entries in the logbook;

associating the third data entry with one of the first data entry and the second data entry; and inputting the third data entry into the logbook with an association with the structured collection procedure in accordance with a rule from the membership rule set.

* * * * *